US00PP20549P2

(12) United States Plant Patent
Mak

(10) Patent No.: US PP20,549 P2
(45) Date of Patent: Dec. 8, 2009

(54) LILY PLANT NAMED 'TINY PADHYE'

(50) Latin Name: *Lilium L.*
Varietal Denomination: Tiny Padhye

(75) Inventor: Nicolaas Aloysius Maria Mak, CA 't Zand (NL)

(73) Assignee: Mak 't Zand B.V., t'Zand (NL)

( * ) Notice: Subject to any disclaimer, the term of this patent is extended or adjusted under 35 U.S.C. 154(b) by 0 days.

(21) Appl. No.: 12/228,270

(22) Filed: Aug. 11, 2008

(51) Int. Cl.
*A01H 5/00* (2006.01)

(52) U.S. Cl. ..... Plt./314

(58) Field of Classification Search ..... Plt./314
See application file for complete search history.

(56) References Cited

OTHER PUBLICATIONS

Upov-rom GTITM Plant Variety Database 2009/01, GTU Jouve Retrieval Software, Citation for Lilium 'Tiny Padhye' one page.*

* cited by examiner

*Primary Examiner*—June Hwu
(74) *Attorney, Agent, or Firm*—C. A. Whealy

(57) ABSTRACT

A new and distinct cultivar of Lily plant named 'Tiny Padhye', characterized by its small to medium plant size; vigorous growth habit; freely flowering habit; white and dark purple bi-colored tepals; and good postproduction longevity.

1 Drawing Sheet

Botanical designation: *Lilium L.*
Cultivar denomination: 'TINY PADHYE'.

BACKGROUND OF THE INVENTION

The present Invention relates to a new and distinct cultivar of Asiatic Hybrid Lily plant, botanically known as *Lilium L.*, and hereinafter referred to by the name 'Tiny Padhye'.

The new Asiatic Hybrid Lily plant is a product of a planned breeding program conducted by the Inventor in 'tZand, The Netherlands. The objective of the breeding program was to develop new potted Asiatic Hybrid Lily plants with erect flowers, attractive flower coloration and good postproduction longevity.

The new Asiatic Hybrid Lily plant originated from a cross-pollination in 1998 of two unnamed proprietary selections of *Lilium L.*, not patented. The new Asiatic Hybrid Lily plant was discovered and selected by the Inventor as a flowering plant from within the resultant progeny of the cross-pollination in a controlled greenhouse environment in 'tZand, The Netherlands in 2001.

Asexual reproduction of the new Asiatic Hybrid Lily plant by bulb scales in a controlled greenhouse environment in 't Zand, The Netherlands since 2001, has shown that the unique features of this new Asiatic Hybrid Lily plant are stable and reproduced true to type in successive generations.

SUMMARY OF THE INVENTION

Plants of the new Asiatic Hybrid Lily have not been observed under all possible environmental conditions. The phenotype may vary somewhat with variations in environment such as temperature and light intensity without, however, any variance in genotype.

The following traits have been repeatedly observed and are determined to be the unique characteristics of 'Tiny Padhye'. These characteristics in combination distinguish 'Tiny Padhye' as a new and distinct cultivar of Asiatic Hybrid Lily plant:

1. Small to medium plant size.
2. Vigorous growth habit.
3. Freely flowering habit.
4. White and purple bi-colored tepals.
5. Good postproduction longevity.

Plants of the new Asiatic Hybrid Lily differ from plants of the female parent selection primarily in flower color as plants of the female parent selection have white-colored flowers.

Plants of the new Asiatic Hybrid Lily differ from plants of the male parent selection in the following characteristics:

1. Plants of the new Asiatic Hybrid Lily are taller than plants of the male parent selection.
2. Plants of the new Asiatic Hybrid Lily are more freely flowering than plants of the male parent selection.

Plants of the new Asiatic Hybrid Lily can be compared to plants of Asiatic Hybrid Lily 'Tiny Sensation', disclosed in U.S. Plant Pat. No. 17,617. Plants of the new Asiatic Hybrid Lily differ from plants of 'Tiny Sensation' in the following characteristics:

1. Plants of the new Asiatic Hybrid Lily are taller than plants of 'Tiny Sensation'.
2. Plants of the new Asiatic Hybrid Lily and 'Tiny Sensation' differ in flower color as plants of 'Tiny Sensation' have yellow and dark red bi-colored flowers.

DESCRIPTION OF THE PHOTOGRAPH

The accompanying colored photograph illustrates the overall appearance of the new Asiatic Hybrid Lily plant, showing the colors as true as it is reasonably possible to obtain in colored reproductions of this type. Colors in the photograph may differ slightly from the color values cited in the detailed botanical description which accurately describe the colors of the new Asiatic Hybrid Lily plant. The photograph comprises a side perspective view of a typical flowering plant of 'Tiny Padhye' grown in a container.

DETAILED BOTANICAL DESCRIPTION

In the following description, color references are made to The Royal Horticultural Society Colour Chart, 2001 Edition, except where general terms of ordinary dictionary significance are used. The aforementioned photograph and following observations and measurements describe plants that had been growing for about five months in 'tZand, The Netherlands under commercial practice in a glass-covered greenhouse. Plants were grown at a minimum temperature of about 15° C. and the average daylength was about 14 hours. Measurements and numerical values represent averages for typical flowering plants. The photograph and the description were taken during the winter.

Botanical classification:

*Lilium L.* 'Tiny Padhye'.

Parentage:

*Female, or seed, parent.*—Unnamed proprietary selection of *Lilium L.*, not patented.

*Male, or pollen, parent.*—Unnamed proprietary selection of *Lilium L.*, not patented.

Plant description:

*Plant form/growth habit.*—Upright flowering plant; single erect flowering stem with a terminal cluster of flowers; small to medium plant size.

*Growth habit.*—Vigorous.

*Plant height, soil level to top of flowers.*—About 44 cm.

*Plant diameter.*—About 20 cm.

*Flowering stems.*—Diameter: About 5 mm. Internode length: About 0.5 cm to 2 cm. Strength: Strong. Texture: Smooth, glabrous. Color: Close to 144B.

*Leaves.*—Arrangement: Alternate; simple; sessile. Quantity of leaves per plant: About 91. Length, lower leaves: About 11.5 cm. Width, lower leaves: About 1.5 cm. Length, upper leaves: About 8 cm. Width, upper leaves: About 1.5 cm. Shape: Lanceolate. Apex: Acute. Base: Decurrent. Margin: Entire. Texture, upper and lower surfaces: Glabrous, smooth; leathery. Venation pattern: Parallel. Color: Developing and fully expanded leaves, upper surface: Close to 137B; venation, close to 137B. Developing and fully expanded leaves, lower surface: Close to 137D; venation, close to 137D.

*Bulbs.*—Diameter: About 10 cm to 20 cm. Texture: Smooth. Color: Close to 155D.

Flower description:

*Flowering habit.*—Terminal single flowers arranged on a raceme on long, mostly erect and strong flowering stems. Flowers face mostly upright.

*Fragrance.*—Slightly fragrant.

*Natural flowering season.*—Plants flower in June and July in The Netherlands. Plants can be flowered year-round in the greenhouse and forced to bloom about 60 days after planting bulbs.

*Flower longevity on the plant.*—About six days; tepals not persistent; gynoecium persistent.

*Flower buds.*—Length: About 8 cm. Diameter: About 3 cm. Circumference: About 9 cm. Shape: Lanceolate. Texture: Slightly pubescent. Color: Close to 145A to 145C brushed with close to 59A; sutures, close to 146A.

*Flowers.*—Quantity of flowers per flowering stem: Freely flowering; larger bulbs will produce plants with about ten flowers per flowering stem. Shape: Funnel-shaped; when fully opened, flowers flatten and reflex slightly. Diameter: About 17.5 cm. Depth (height): About 3 cm.

*Perianth.*—Quantity/arrangement: Six tepals per flower; tepals imbricate. Tepal length, inner tepals: About 7.5 cm. Tepal width, inner tepals: About 5 cm. Tepal length, outer tepals: About 8.5 cm. Tepal width, outer tepals: About 4 cm. Tepal shape: Lanceolate. Tepal apex: Acute. Tepal margin: Entire. Tepal texture, upper and lower surfaces: Smooth, glabrous. Tepal color: When opening, upper and lower surfaces: Towards the apex, more white than 157D; towards the base and along the central margins, close to 187A. Fully opened, upper and lower surfaces: Towards the apex, more white than 157D; towards the base and along the central margins, close to 187A.

*Pedicels.*—Angle: About 45° to 70° from vertical. Strength: Strong. Length: About 6 cm. Diameter: About 1 cm. Texture: Smooth, glabrous. Color: Close to 143B.

*Reproductive organs.*—Stamens: Quantity per flower: About six. Filament length: About 5 cm. Filament color: Close to 157C. Anther length: About 1 cm. Anther color: Close to 23A. Pollen color: Close to 23A. Pistils: Quantity per flower: One. Style length: About 4.5 cm. Style color: Close to 154C. Stigma length: About 5 mm. Stigma color: Close to 13C.

*Fruits.*—Length: About 1.5 cm. Diameter: About 5 mm. Color: Close to 187A.

*Seed produced.*—No viable seeds observed.

Disease/pest resistance: Resistance to pathogens and pests common to Asiatic Hybrid Lilies has not been observed.

Garden performance: Plants of the new Asiatic Hybrid Lily have exhibited good tolerance to rain and wind and have been observed to tolerate temperatures from about −15° C. to about 40° C.

It is claimed:

1. A new and distinct Lily plant named 'Tiny Padhye' as illustrated and described.

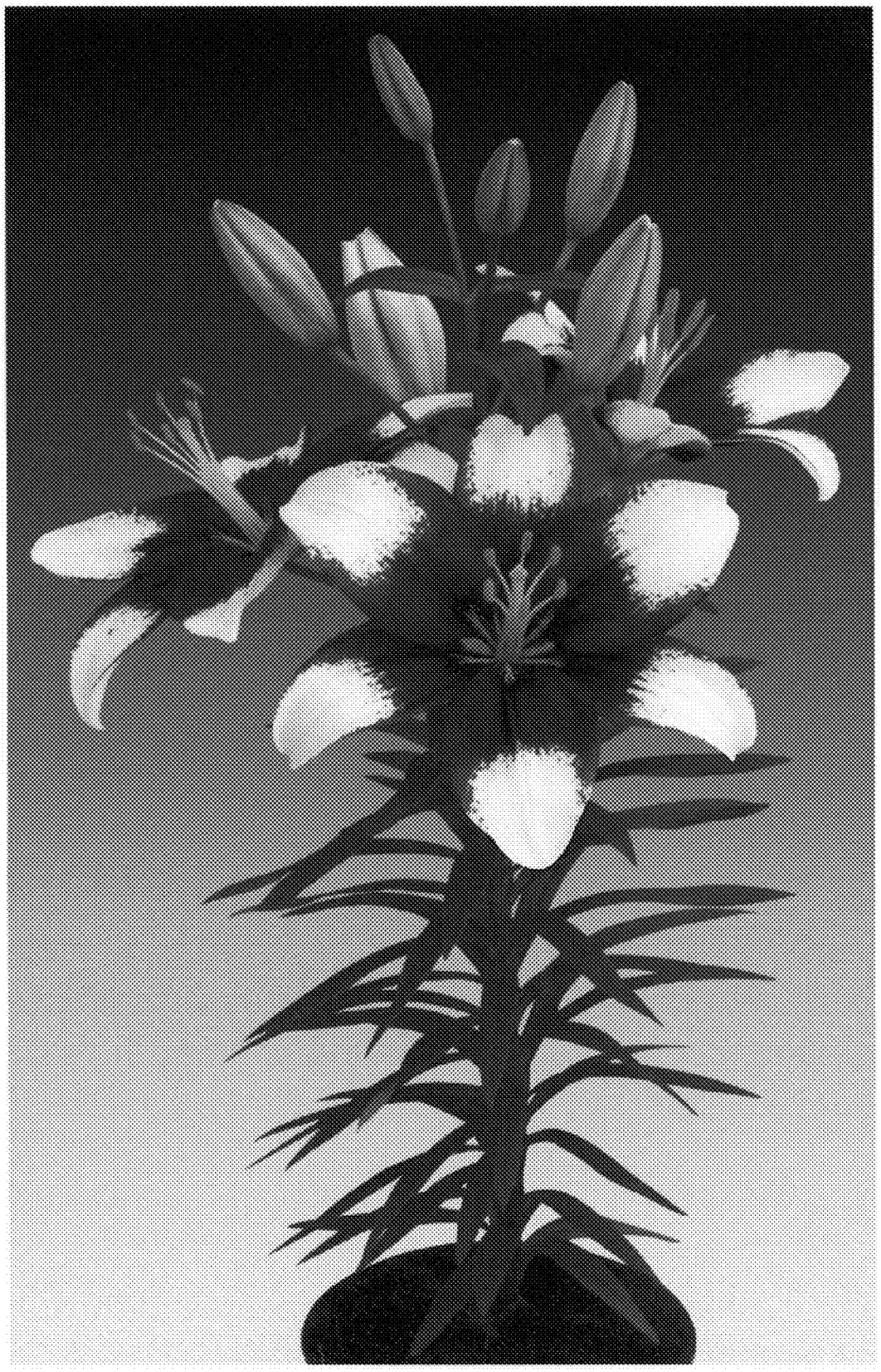

* * * * *